(12) United States Patent
Jumaa et al.

(10) Patent No.: US 11,642,072 B2
(45) Date of Patent: May 9, 2023

(54) TELESTROKE EYE EXAMINATION ACCESSORY

(71) Applicant: The University of Toledo, Toledo, OH (US)

(72) Inventors: Mouhammad A. Jumaa, Toledo, OH (US); Syed F. Zaidi, Toledo, OH (US); Hisham Salahuddin, Toledo, OH (US)

(73) Assignee: The University of Toledo, Toledo, OH (US)

( * ) Notice: Subject to any disclaimer, the term of this patent is extended or adjusted under 35 U.S.C. 154(b) by 589 days.

(21) Appl. No.: 16/783,608

(22) Filed: Feb. 6, 2020

(65) Prior Publication Data
US 2020/0253532 A1 Aug. 13, 2020

Related U.S. Application Data

(60) Provisional application No. 62/802,268, filed on Feb. 7, 2019.

(51) Int. Cl.
| | |
|---|---|
| *A61B 5/00* | (2006.01) |
| *G16H 40/67* | (2018.01) |
| *A61B 3/14* | (2006.01) |
| *A61B 3/113* | (2006.01) |
| *A61B 3/00* | (2006.01) |
| *H04N 5/33* | (2023.01) |

(52) U.S. Cl.
CPC .......... *A61B 5/4064* (2013.01); *A61B 3/0033* (2013.01); *A61B 3/113* (2013.01); *A61B 3/14* (2013.01); *A61B 5/002* (2013.01); *A61B 5/0013* (2013.01); *A61B 5/4863* (2013.01); *A61B 5/6803* (2013.01); *G16H 40/67* (2018.01); *H04N 5/33* (2013.01)

(58) Field of Classification Search
CPC ..... A61B 5/4064; A61B 3/0033; A61B 3/113; A61B 3/14; A61B 5/0013; A61B 5/002; A61B 5/4863; A61B 5/6803; A61B 3/145; A61B 3/024; A61B 5/163; A61B 5/0077; G16H 40/67; G16H 50/20; G16H 40/63; H04N 5/33
USPC ........................................................ 351/206
See application file for complete search history.

(56) References Cited

U.S. PATENT DOCUMENTS

| | | | |
|---|---|---|---|
| 6,288,717 B1 * | 9/2001 | Dunkle ............... | G06F 16/9535 715/764 |
| 6,361,167 B1 * | 3/2002 | Su .......................... | A61B 3/107 351/206 |
| 2002/0060778 A1 * | 5/2002 | Su .......................... | A61B 3/154 351/206 |

(Continued)

*Primary Examiner* — Mohammed A Hasan
(74) *Attorney, Agent, or Firm* — MacMillan, Sobanski & Todd, LLC

(57) ABSTRACT

A telestroke eye examination accessory device, a system incorporating the same, and methods of using the same, are described. The telestroke eye examination accessory device includes eyewear having a first eye well and a second eye well, a first camera positioned within the first eye well, a second camera positioned within the second eye well, a first light array having lights in each of four different quadrants in the first eye well, and a second light array having lights in each of four different quadrants in the second eye well. The system further includes a graphical user interface useful for a practitioner using the telestroke eye examination accessory device to assess the field of vision of a patient wearing the eyewear.

19 Claims, 20 Drawing Sheets

(56) References Cited

U.S. PATENT DOCUMENTS

| | | | | |
|---|---|---|---|---|
| 2004/0114108 A1* | 6/2004 | Niven | ............... | A61B 3/107 |
| | | | | 351/212 |
| 2006/0111620 A1* | 5/2006 | Squilla | ............... | A61B 5/00 |
| | | | | 600/300 |
| 2009/0306741 A1* | 12/2009 | Hogle | ............ | A61N 1/36103 |
| | | | | 600/595 |
| 2016/0270656 A1* | 9/2016 | Samec | ............... | A61B 3/063 |

* cited by examiner

TELESTROKE EYE EXAMINATION ACCESSORY

RELATED APPLICATIONS

This application claims priority to U.S. Provisional Application No. 62/802,268 filed under 35 U.S.C. § 111(b) on Feb. 7, 2019, the disclosure of which is incorporated herein by reference in its entirety.

STATEMENT REGARDING FEDERALLY SPONSORED RESEARCH

This invention was made with no government support. The government has no rights in this invention.

BACKGROUND

A large percentage of acute ischemic stroke cases are triaged via telemedicine. Some strokes present with visual symptoms or vertigo with visual disturbances. However, it is difficult to assess posterior circulation strokes via telemedicine. Curative, time-sensitive treatment is sometimes withheld due to inaccurate evaluation. Thus, there is a need in the art for new and improved devices, systems, and methods for evaluating patients for symptoms of strokes.

SUMMARY

Provided is a telestroke eye examination accessory device comprising eyewear configured to be mounted on a patient's head, the eyewear comprising a frame defining a first eye well and a second eye well, a first camera in the first eye well, a first light array in the first eye well, wherein the first light array comprises a light in each of four different quadrants within the first eye well, a second camera in the second eye well, and a second light array in the second eye well, wherein the second light array comprises a light in each of four different quadrants within the second eye well.

In certain embodiments, the telestroke eye examination accessory device further comprises an LED controller configured to control the first light array and the second light array. In certain embodiments, the telestroke eye examination accessory device further comprises a USB hub or USB connector port. In certain embodiments, the telestroke eye examination accessory device further comprises a power source configured to supply power to the first camera, the second camera, the first light array, and the second light array.

In certain embodiments, the first camera and the second camera are each IR cameras.

In certain embodiments, the first light array comprises LED lights, and the second light array comprises LED lights.

In certain embodiments, the first camera is positioned along a first centerline within the first eye well, and the second camera is positioned along a second centerline within the second eye well. In particular embodiments, the first light array comprises two lights along the first centerline, and the second light array comprises two lights along the second centerline.

In certain embodiments, the telestroke eye examination accessory device further comprises a darkening cover disposed on the eyewear frame. In certain embodiments, the telestroke eye examination accessory device further comprises a darkening cover disposed on the eyewear frame such that the first camera, second camera, first light array, and second light array are disposed between the eyewear frame and the darkening cover.

In certain embodiments, the telestroke eye examination accessory device further comprises a light-occluding cowl.

In certain embodiments, the telestroke eye examination accessory device is configured to communicate wirelessly with a telemedicine system. In particular embodiments, the telestroke eye examination accessory device is configured to communicate with the telemedicine system via Bluetooth connection.

In certain embodiments, the first camera is configured to observe a first eye of a patient wearing the eyewear, and the second camera is configured to observe a second eye of the patient wearing the eyewear.

In certain embodiments, the first camera is equidistant from each of the four lights of the first light array, and the second camera is equidistant from each of the four lights of the second light array.

In certain embodiments, the telestroke eye examination accessory device further comprises temples connected to the frame for securing the eyewear on the patient's head. In certain embodiments, the eyewear comprises goggles that create darkness within the first eye well and the second eye well.

In certain embodiments, the first camera and the second camera are tracking cameras configured to identify abnormal eye movements. In particular embodiments, vestibular testing algorithms are configured to provide objective data on abnormal eye movements and simplified visual field testing using a central fixation point Further provided is a system for telemedicine comprising a telestroke eye examination accessory device, a smart device in communication with the telestroke eye examination accessory device, and a graphical user interface on the smart device displaying information obtained from the telestroke eye examination accessory device, wherein the telestroke eye examination accessory device is capable of wireless communications. In certain embodiments, the telestroke eye examination accessory device comprises eyewear having two eye wells, each eye well comprising a camera and lights in each of four quadrants within the eye well.

Further provided is a system for telemedicine comprising a device comprising a graphical user interface displaying information about a patient, and eyewear in communication with the device, wherein the eyewear is configured to illuminate lights and provide to the graphical user interface a live stream of the patient's eyes while wearing the eyewear. In certain embodiments, a user may control the illumination of lights within the eyewear through the graphical user interface. In certain embodiments, the eyewear communicates wirelessly to the device. In certain embodiments, the live stream is provided by IR cameras within the eyewear.

In certain embodiments, the eyewear comprises tracking cameras configured to identify abnormal eye movements. In particular embodiments, the system further comprises software having vestibular testing algorithms for obtaining objective data on abnormal eye movements and simplifying visual field testing using a central fixation point. In certain embodiments, the method further comprises artificial intelligence algorithms configured to evaluate trackable eye movements of the patient's eyes to detect different types of nystagmus, skew deviation, or subtle gaze abnormalities.

BRIEF DESCRIPTION OF THE DRAWINGS

The patent or application file may contain one or more drawings executed in color and/or one or more photographs.

Copies of this patent or patent application publication with color drawing(s) and/or photograph(s) will be provided by the U.S. Patent and Trademark Office upon request and payment of the necessary fees.

DETAILED DESCRIPTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

There is a growing demand for telemedicine, especially in the context of stroke evaluation because of the limited number of stroke specialists. However, it is difficult to assess visual fields and monitor eye movements via telemedicine. Often, practitioners rely on a nurse or other assistant at the bedside of the patient to help with an assessment of the patient's vision. However, doing so has reliability issues.

Provided herein is a device that solves these issues by providing the practitioner with a tool for accurately assessing visual fields and monitoring eye movements without relying on a person at the bedside of the patient. In particular, provided herein is a telestroke eye examination accessory device that, in general, includes head-mounted eyewear having light arrays and cameras pointed at the eyes of the wearer, with the capability of providing a live stream of the patient's eyes while their field of vision is being tested with the light arrays. The telestroke eye examination accessory device allows a practitioner to remotely assess a patient's field of vision without relying on other personnel to observe the patient's eye movements.

Figure 1:
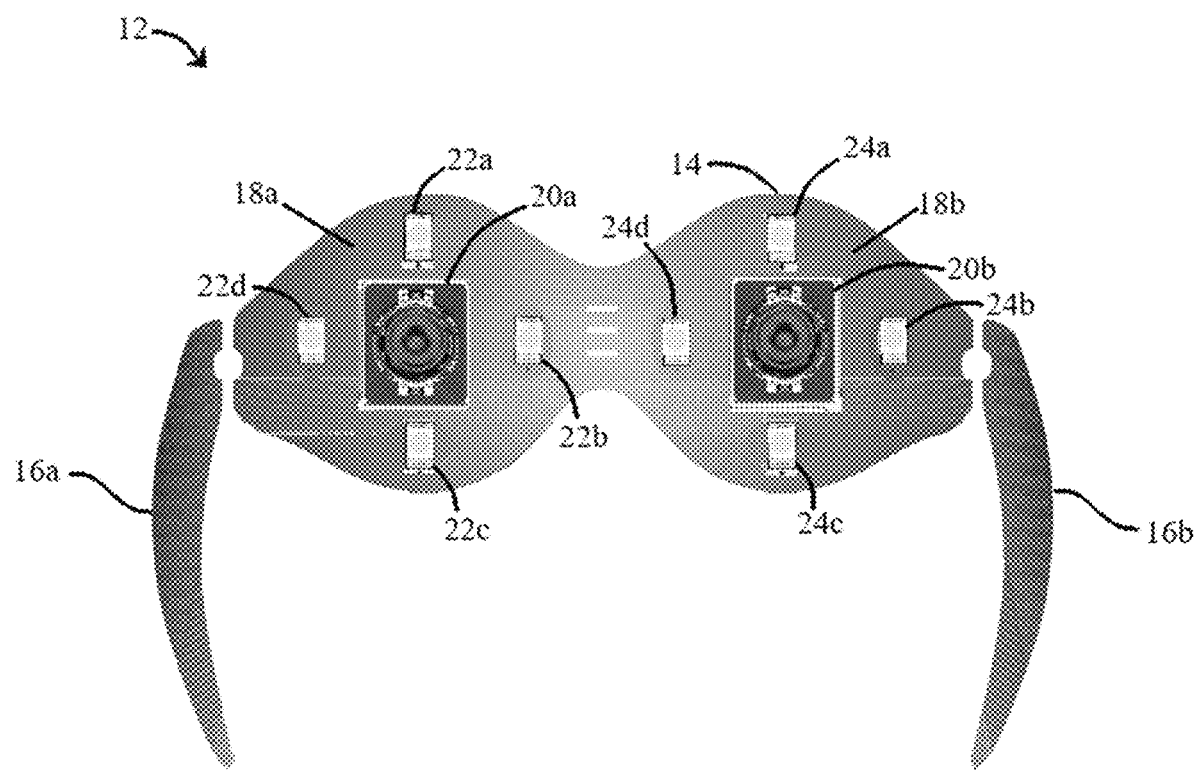
FIG. 1 Illustration of an embodiment of a telestroke eye examination accessory device in accordance with the present disclosure.

A telestroke eye examination accessory device in accordance with the present disclosure generally includes eyewear configured to be worn by the patient being assessed. Referring now to FIG. 1, an embodiment of eyewear 12 for a telestroke eye examination accessory device is depicted, without a darkening cover 26. The eyewear 12, such as goggles or glasses, is constructed on a suitable frame 14 with temples 16a, 16b configured to hold the eyewear 12 in place on a patient's head. The frame 14 is configured to be worn and may be adjusted to face size. The eyewear frame 14 may be made of polycarbonate glass or other suitable material.

Figure 2:
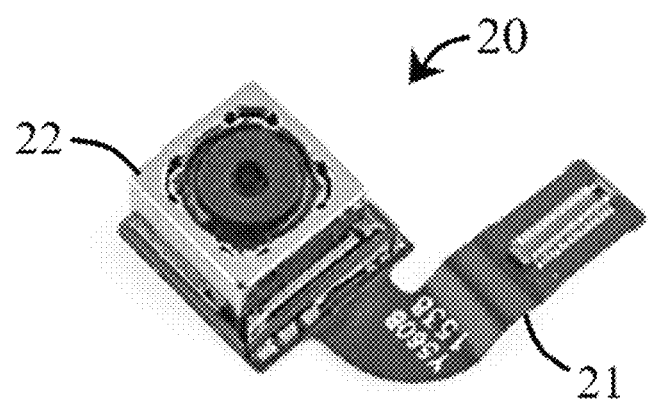
FIG. 2 Non-limiting example of a camera useable in a telestroke eye examination accessory device in accordance with the present disclosure.

Referring still to FIG. 1, the eyewear 12 has a first eye well 18a and a second eye well 18b. The first eye well 18a includes a first camera 20a, which may be positioned along the centerline in the first eye well 18a so as to be configured to observe directly into the center of a first eye of a patient wearing the eyewear 12. The second eye well 18b includes a second camera 20b, which may be positioned along the centerline in the second eye well 18b so as to be configured to observe directly into the center of a second eye of a patient wearing the eyewear 12. The first camera 18a and the second camera 18b may be, for example, IR cameras so as to work well under low-light conditions in order to observe eye movements of a patient wearing the eyewear 12. The cameras 20a, 20b may be miniature cameras, small enough to fit inside the eye wells 18a, 18b while leaving room for the light arrays 22, 24. A non-limiting example of a suitable camera 20 is depicted in FIG. 2. As seen in FIG. 2, a camera 20 may include a cable 21 for connection to a power source. However, other types of cameras are suitable and are nonetheless encompassed within the scope of the present disclosure. The cameras 20a, 20b may further include a tracking ability so as to enable the practitioner to identify abnormal eye movements. Companion software may include vestibular testing algorithms that provide objective data on abnormal eye movements and simplified visual field testing using a central fixation point.

Referring still to FIG. 1, the device further includes a first light array composed of at least four lights 22a, 22b, 22c, 22d in the first eye well 18a. The first light array includes a light 22a, 22b, 22c, 22d in each of four different quadrants of the first eye well 18a. As a non-limiting example, a light 22a is disposed above the first camera 20a, a light 22b is disposed to the right of the first camera 20a, a light 22c is disposed below the first camera 20a, and a light 22d is disposed to the left of the first camera 20a. Each of the lights 22a, 22b, 22c, 22d of the first light array may be equidistant from the first camera 20a. However, other arrangements of the lights 22a, 22b, 22c, 22d within four quadrants of the first eye well 18a are possible and nonetheless encompassed within the present disclosure.

Similarly, the eyewear 12 further includes a second light array composed of at least four lights 24a, 24b, 24c, 24d in the second eye well 18b. The second light array includes a light 24a, 24b, 24c, 24d in each of four different quadrants of the second eye well 18b. As a non-limiting example, a light 24a is disposed above the first camera 20b, a light 24b is disposed to the right of the first camera 20b, a light 24c is disposed below the first camera 20b, and a light 24d is disposed to the left of the first camera 20b. Each of the lights 24a, 24b, 24c, 24d of the second light array may be equidistant from the second camera 20b. However, other arrangements of the lights 24a, 24b, 24c, 24d within four quadrants of the second eye well 18b are possible and nonetheless encompassed within the present disclosure.

Figure 3:
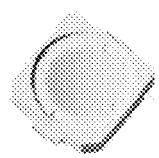
FIG. 3 Non-limiting example of a micro LED usable in the light arrays of a telestroke eye examination accessory device in accordance with the present disclosure.

The lights 22a, 22b, 22c, 22d of the first light array and the lights 24a, 24b, 24c, 24d of the second light array may be, for example, micro LEDs. A non-limiting example of a suitable LED is depicted in FIG. 3. However, other types of lights are suitable and are nonetheless encompassed within the scope of the present disclosure. The lights 22a-22d, 24a-24d may have a predefined shape. The lights 22a, 22b, 22c, 22d, 24a, 24b, 24c, 24d of the light arrays 22, 24 may be individually controlled with on/off functions, and also may have individual brightness control. The on/off status and the brightness of each of the lights 22a, 22b, 22c, 22d, 24a, 24b, 24c, 24d may be controlled through a graphical user interface on a smart device in communication with the eyewear 12, as will be described in more detail later. The light arrays 22, 24 may be communicatively coupled to an LED controller or other processor.

Figure 4:
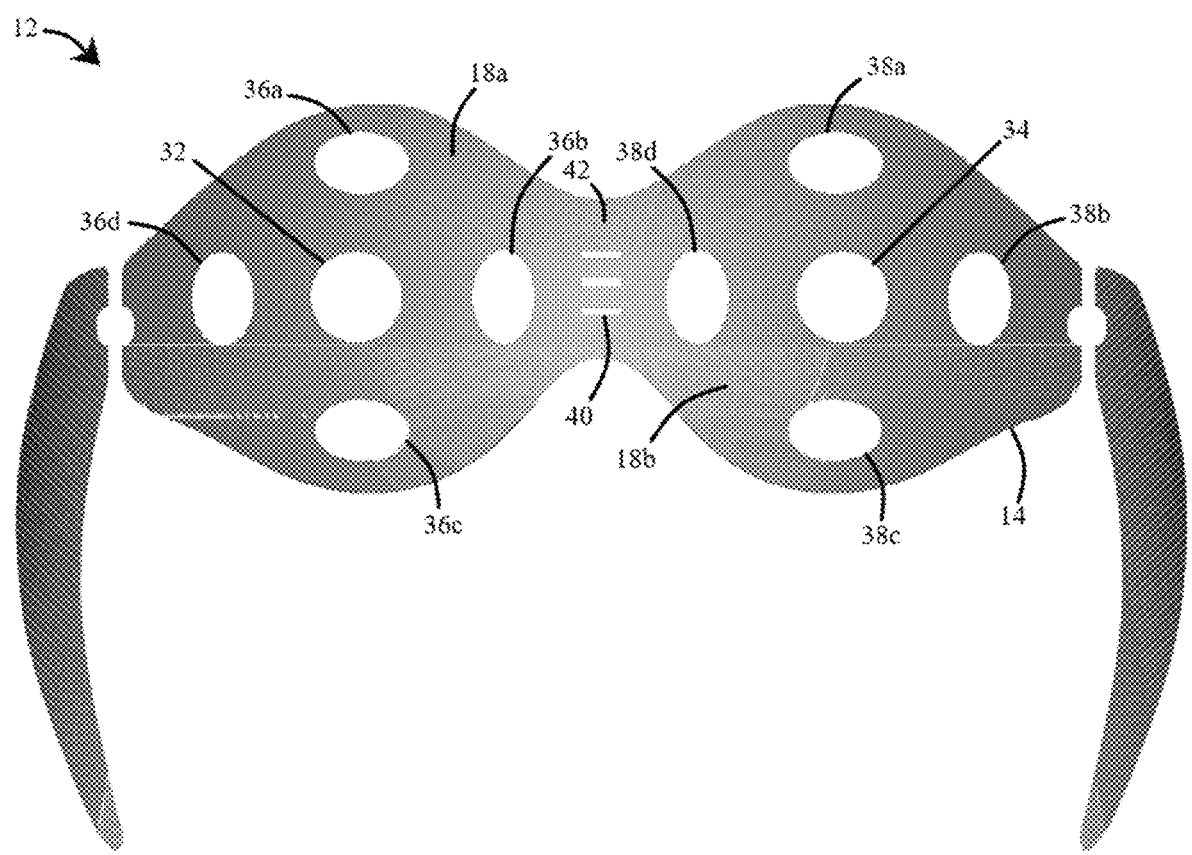
FIG. 4 Illustration of eyewear for a telestroke eye examination accessory device in accordance with the present disclosure.

Referring now to FIG. 4, the eyewear 12 is depicted without the lights 22a-22d, 24a-24d and cameras 20a, 20b inserted into the eyewear frame 14. The eyewear frame 14 includes a first camera slot 32 configured to house the first camera 20a and a second camera slot 34 configured to house the second camera 20b. The eyewear frame 14 further includes four first light array slots 36a, 36b, 36c, 36d in the first eye well 18a configured to house the first light array lights 22a, 22b, 22c, 22d, and four second light array slots 38a, 38b, 38c, 38d in the second eye well 18b configured to house the second light array lights 24a, 24b, 24c, 24d. The eyewear frame 14 may further include one or more cable slots 40, such as in the nose section 42 of the eyewear frame 14, configured to allow the passage of cables (such as the cables 21 of the cameras 20a, 20b) from the cameras 20a, 20b and/or lights 22a-22d, 24a-24d through the frame 14 to hardware such as a light mixer 28 or a power source.

Figure 5:
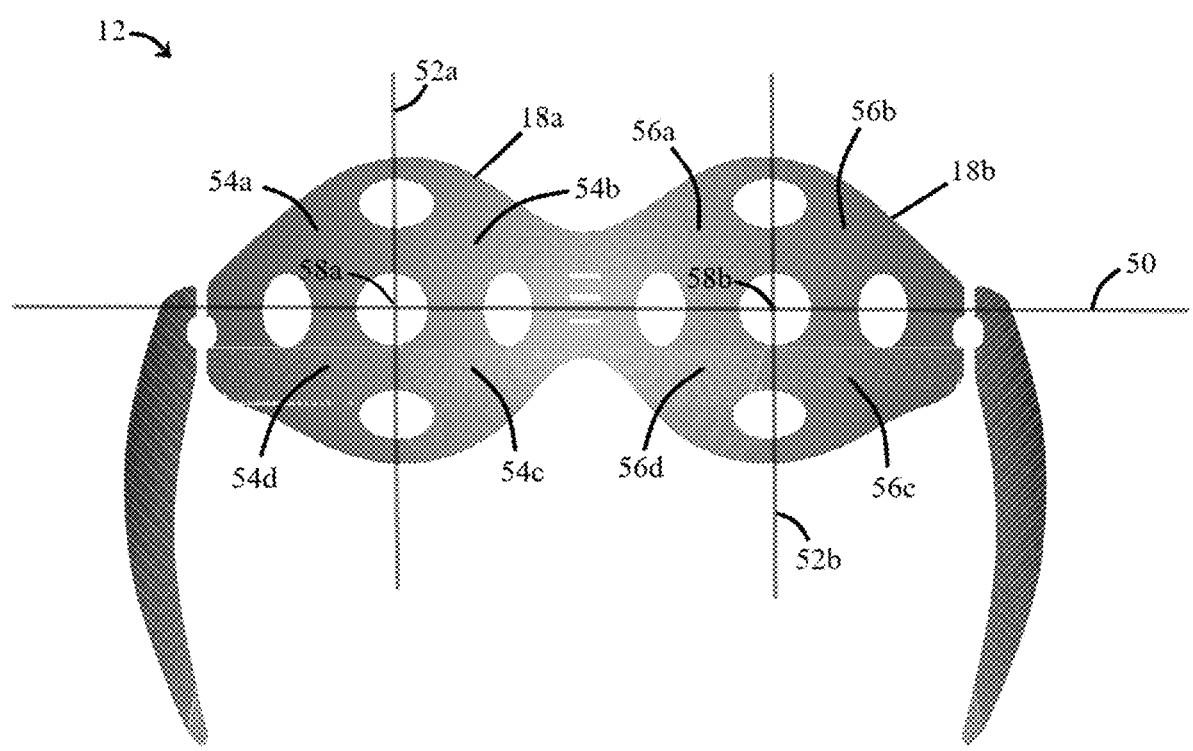
FIG. 5 Illustration of eyewear for a telestroke eye examination accessory device in accordance with the present disclosure.

The lights 22a-22d, 24a-24d may be used to illuminate around the eyes of a patient wearing the eyewear 12 to examine visual fields of the patient wearing the eyewear 12. As noted above, the lights 22a-22d, 24a-24d are disposed in four different quadrants within the respective eye well 18a, 18b of the eyewear 12. Referring now to FIG. 5, the four quadrants of each eye well 18a, 18b may be defined by an imaginary horizontal centerline 50 and two imaginary vertical centerlines 52a, 52b. The horizontal centerline 50 bisects the eyewear 12 through the center of the first camera slot 32 and the center of the second camera slot 34. The first vertical centerline 52a runs through the first light array slot 36a, the first camera slot 34, and the first light array slot 36c. The first vertical centerline 52a intersects the horizontal centerline 50 at point 58a. The second vertical centerline 52b runs through the second light array slot 38a, the second camera slot 34, and the second light array slot 38c. The second vertical centerline 52b intersects the horizontal centerline 50 at point 58b. In this manner, the lights 22a-22d, 24a-24d of the light arrays may be arranged in four different quadrants in each eye well 18a, 18b by arranging each of two lights 22b, 22d along the centerline 50 the same distance away from the point of intersection 58a, and arranging each of two lights 22a, 22c along the vertical centerline 52a, 52b the same distance away from the point of intersection 58a. Similarly, each of two lights 24b, 24d may be arranged along the horizontal centerline 50 the same distance away from the point of intersection 58b, and each of two lights 24a, 24c may be arranged along the second vertical centerline 52b the same distance away from the point of intersection 58b.

Alternatively, referring still to FIG. 5, the four quadrants may be defined such that the lights 22a-22d, 24a-24d are not vertically and horizontally aligned with the cameras 20a, 20b. For example, the four quadrants in the first eye well 18a may include two above the horizontal centerline 50, and two below the horizontal centerline 50, one on each side of the respective vertical center line 52a, 52b above and below the horizontal centerline 50. Thus, in the first eye well 18a, a first quadrant 54a may be above the horizontal centerline 50 and to the left of the vertical centerline 52a, a second quadrant 54b may be above the horizontal centerline 50 and to the right of the vertical centerline 52a, a third quadrant 54c may be below the horizontal centerline 50 and to the right of the vertical centerline 52a, and a fourth quadrant 54d may be below the horizontal centerline 50 and to the left of the vertical centerline 52a. Similarly, in the second eye well 18b, a first quadrant 56a may be above the horizontal centerline 50 and to the left of the vertical centerline 52b, a second quadrant 56b may be above the horizontal centerline 50 and to the right of the vertical centerline 52b, a third quadrant 56c may be below the horizontal centerline 50 and to the right of the vertical centerline 52b, and a fourth quadrant 56d may be below the horizontal centerline 50 and to the left of the vertical centerline 52b.

The above examples of four-quadrant arrangements of the lights 22a-22d, 24a-24d are merely non-limiting examples of how the four quadrants of each eye well 18a, 18b may be defined. Many other configurations are possible and are nonetheless encompassed within the scope of the present disclosure. As the skilled person will recognize, what is important for the arrangement of the lights 22a-22d, 24a-24d within the eye wells 18a, 18b is that they are adequately spaced out around sufficient places within the eye wells 18a, 18b so as to provide the practitioner with useful information regarding a patient's field of vision. Furthermore, though four quadrants are referred to herein for exemplary purposes, the light arrays may each individually include more than four lights, where such lights are disposed in more than four quadrants within the respective eye well 18a, 18b. For example, the light arrays may each include six lights, arranged in six different quadrants within the respective eye well 18a, 18b. The number of lights in the light arrays and the number of quadrants in the eye wells 18a, 18b within which the lights are arranged, are not particularly limited so long as the arrangement of the lights of the light arrays within the eyewear 12 provides the practitioner with useful information regarding the patient's field of vision.

Figure 6:
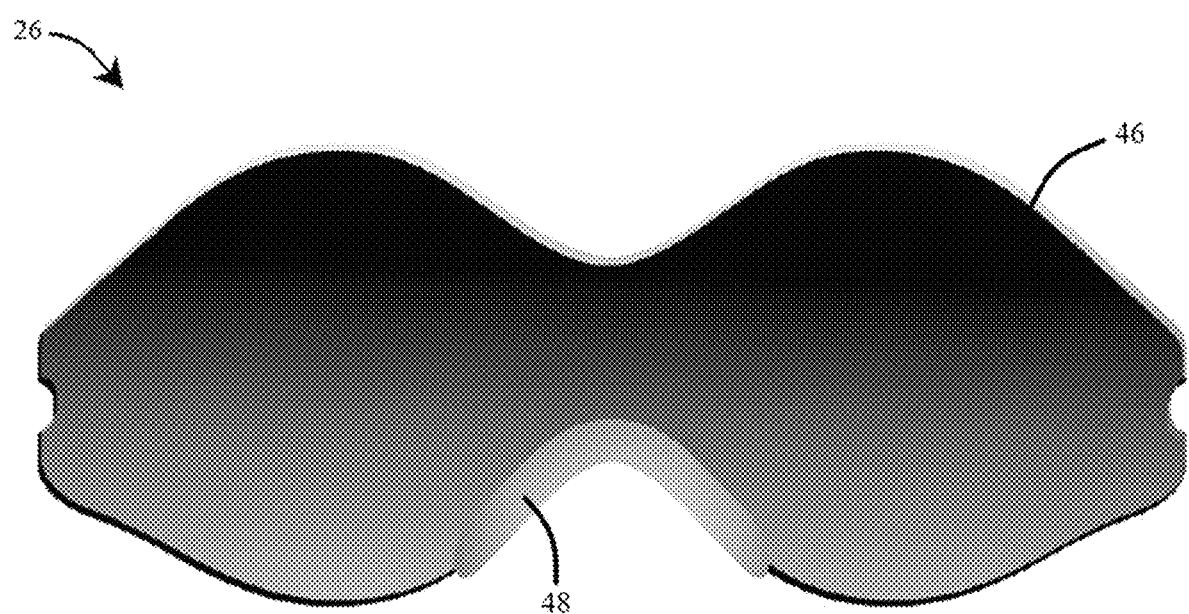
FIG. 6 Illustration of a darkening cover of a telestroke eye examination accessory device in accordance with the present disclosure.

Referring now to FIG. 6, a darkening cover 26 is depicted. The darkening cover 26 may include an eyewear-shaped frame 46 composed of a substantially opaque material, such as a suitable plastic or glass, and a nose piece 48 composed of a soft material configured to rest comfortably on a patient's nose. The darkening cover 26 may mirror the shape of the eyewear 12. The darkening cover 26 may be placed behind the cameras 20a, 20b and light arrays 22, 24 with respect to the patient, so as to block out light. Together, the eyewear frame 14 and the darkening cover 26 make up a wearable optical assembly. Furthermore, a light-occluding cowl may be disposed around the eyewear 12 to further prevent light from entering when worn.

Alternatively or in addition, a darkening cover 26 may be placed over the eyewear frame 14 so as to hide the cameras and light arrays (when not illuminated) from the patient's view. In this manner, the darkening cover 26 may be disposed on the eyewear frame 14 such that the first camera 20a, second camera 20b, first light array lights 22a-22d, and second light array lights 24a-24d are disposed between the eyewear frame 14 and the darkening cover 26. Thus, while the eyewear 12 is being worn by the patient, the patient generally observes only darkness until the lights 22a-22d, 24a-24d of the light arrays 22, 24 are illuminated.

Alternatively, the eyewear 12 can be incorporated into fitted goggles that create darkness within each eye well 18a, 18b to allow visual field testing with the lights 22a-22d, 24a-24d.

The eyewear 12 may further include various components for providing wireless communications ability. For example, the eyewear 12 may be capable of wireless communications, such as through a Bluetooth connection, with a smart device or a telemedicine system.

Figure 7:
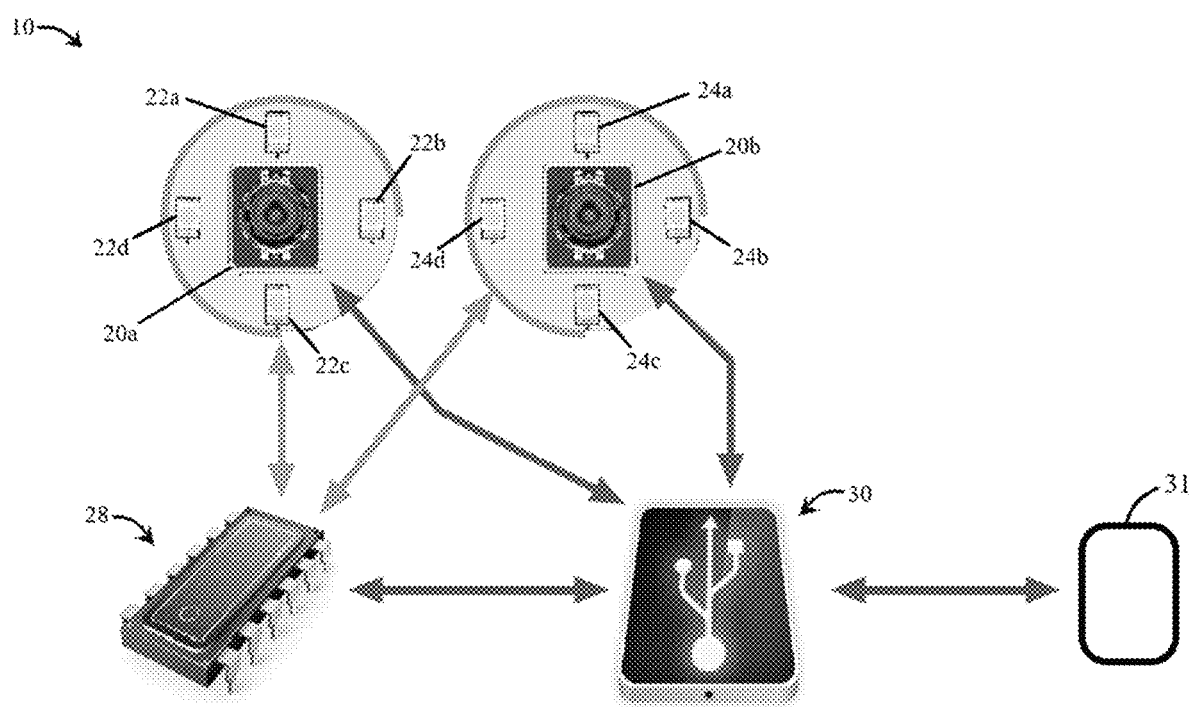
FIG. 7 Illustration of components of a system for telemedicine showing communicative coupling between LEDs, cameras, a controller, and a USB hub.

Referring now to FIG. 7, components of a system 10 for conducting telemedicine that includes the eyewear 12 are illustrated. For simplicity of illustration, the full eyewear 12 is not depicted in FIG. 7. Each of the lights 22aa-22d, 24a-24d may be controlled by a light mixer 28 which may be mounted within the eyewear 12 or may alternatively be external to the eyewear 12 and connected thereto through a suitable cable. The light mixer 28 may be any suitable processor and may be communicatively coupled to a USB hub 30, which may be in wireless communication with a smart device 31 such as a phone or tablet. The USB hub 30 may also be mounted within the eyewear 12 or may alternatively be external to the eyewear 12. The eyewear 12 may also include USB ports through which the eyewear 12 may be wired via USB cable to a device such as a tablet or PC.

The eyewear 12 may further include a suitable power source configured to supply power to the first camera 20a, the second camera 20b, the first light array lights 22a-22d, and the second light array lights 24a-24d. The power source may be, for example, a lithium polymer battery or other rechargeable battery. A charger may be fixed to the eyewear 12. Alternatively, the light arrays lights 22a-22d, 24a-24a and cameras 20a, 20b may be powered by USB through the USB hub 30, or a battery which powers the light arrays 22, 24 and cameras 20a, 20b may be charged by USB through the USB hub 30. In such cases, the light array lights 22a-22d, 24a-24d, and/or cameras 20a, 20b may be wired to the USB hub 30, which may then be plugged into a power outlet or computing device with a USB cable so as to supply power to the USB hub 30 and, in turn, light arrays lights 22a-22d, 24a-24d, and/or cameras 20a, 20b. Thus, the eyewear 12 may include one or more USB ports. However, other power sources are possible and are nonetheless encompassed within the scope of the present disclosure. The eyewear 12 may further include a WiFi adapter.

Figure 8:
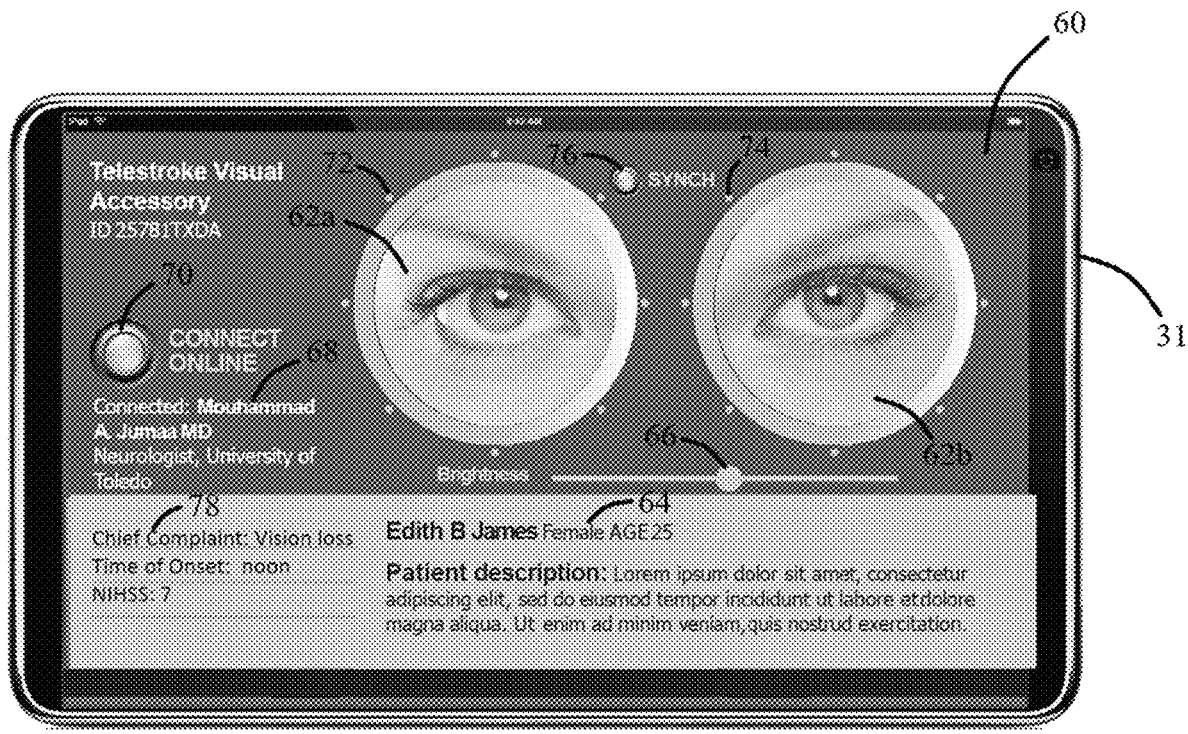
FIG. 8 Illustration of a graphical user interface displayed on a smart device connected to a telestroke eye examination accessory device.
Figure 9:
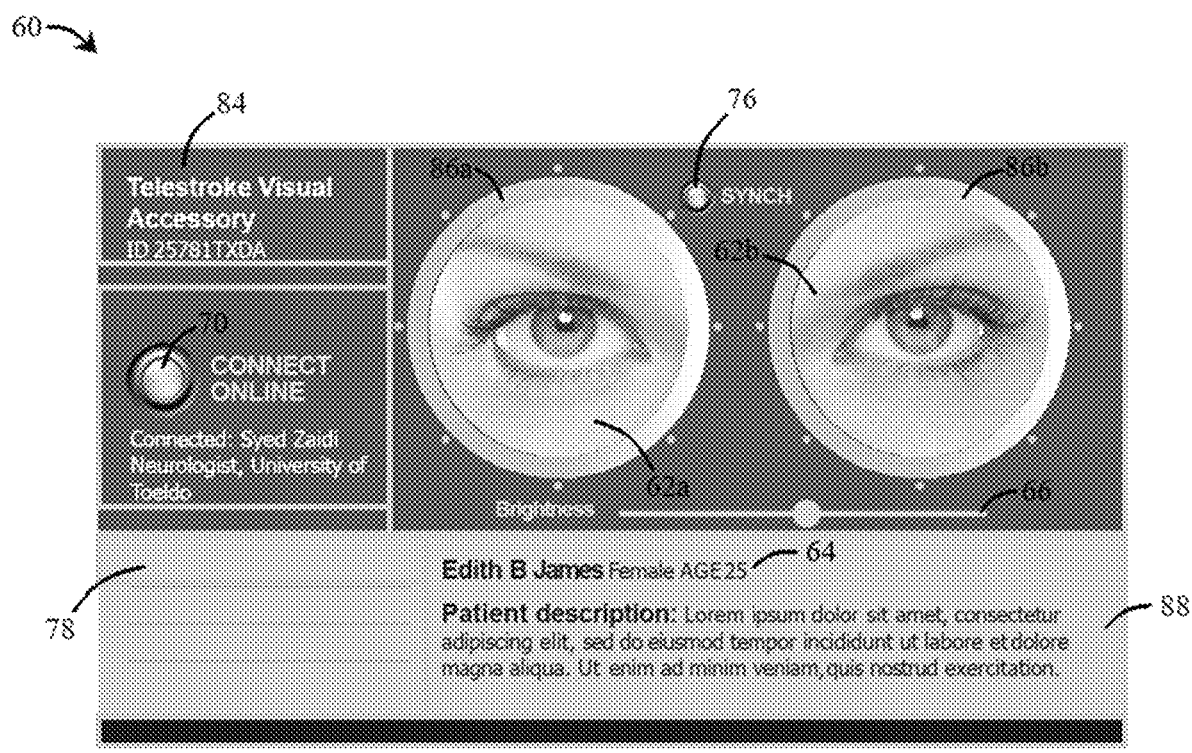
FIG. 9 Illustration of a graphical user interface displayed on a smart device connected to a telestroke eye examination accessory device.

In use, the first and second cameras 20a, 20b may stream live images of the eyes of the patient wearing the eyewear 12 to a smart device 31 running an application which produces a graphical user interface (GUI) 60, as depicted for instance in FIGS. 8-9. A practitioner may connect remotely to the eyewear 12 with the smart device 31 and through the application control the light array lights 22a-22d, 24a-24d, and the cameras 20a, 20b. By causing lights in four different quadrants of each eye well 18a, 18b to be illuminated, and instructing the patient to identify the illuminated lights while keep their eyes looking straight ahead, the practitioner may assess the patient's field of vision. The first camera 20a and the second camera 20b may be useful for ensuring that the patient's eyes remain centered during testing. If, for example, a practitioner observes the patient's eyes moving in order to see the lights illuminated in different quadrants, it may be a sign that the patient is having problems with their vision.

In some embodiments, the system 10 may further include one or more memory components, allowing the system 10 to record eye movements by communication between the cameras 20a, 20b and the memory components.

As noted above, the light array lights 22a-22d, 24a-24d and cameras 20a, 20b may be controlled by software, such as an app run by the practitioner using the software on a suitable device 31 such as smart phone or tablet. As a non-limiting example, the software may include a graphical user interface as depicted in FIGS. 8-9. The software may perform a wide variety of functions, such as, for example, control the cameras, control the light arrays, provide synchronized or independent L/R control, provide network capability (slave mode), provide data entry for visual field findings, and provide data entry for eye movements/nystagmus. The software may be run as an app or, alternatively, as a web application in a browser. For the user end, the software may be written in HTML5 and JSON, for example, and rendered as apps for android and iOS platforms. For the back end, the software may be MySQL running on a custom Linux server with a web based interface for user and subscription management, customer support, and app management.

Referring now to FIG. 8, a GUI 60 may be displayed on a smart device 31. The GUI 60 may be run as an iOS, android, or windows application. The GUI 60 may display the live stream images 62a, 62b of the patient's eyes from the first camera 20a and the second camera 20b. The GUI 60 may display biographical information 64 about the patient. The GUI 60 may provide a brightness control slider 66 configured to control the brightness levels of one or both of the cameras 20a, 20b. The GUI 60 may include provider information 68 about the practitioner using the system 10 to assess the patient. The GUI 60 may include a status indicator light 70 to indicate when the system 10 is online. The GUI 60 may include first light array on/off toggles 72 and second light array on/off toggles 74. The GUI 60 may include a light synchronization switch 76 which controls synchronization of the first light array lights 22a-22d and the second light array lights 24a-24d. The GUI 60 may display symptom or vital signs information 78 to inform the practitioner of the patient's symptoms.

Referring now to FIG. 9, the GUI 60 may display a unique identifier 84. The GUI 60 may allow for controlling the lights 22a-22d, 24a-24d with light dials 86a, 86b that surround the live stream images 62a, 62b of the patient's eyes. The light dials 86a, 86b may be swiped to control the light direction. The brightness control slider 66 may be displayed below the live stream images 62a, 62b. The cameras 20a, 20b may be configured by touching the live stream images 62a, 62b on the GUI 60.

In FIG. 9, there is seen a vital signs information area 78 displayed as being empty. The practitioner using the system 10 may make notes in the vital signs information area 78. Similarly, a description area 88 may be displayed below the patient information 64 and display relevant information about the patient. The practitioner using the system 10 may edit the description area 88.

The system 10 may include software which provides for wireless communication with a telemedicine system, or other smart device. The software may include vestibular testing algorithms for obtaining objective data on abnormal eye movements and simplifying visual field testing using a central fixation point. The software may further include artificial intelligence algorithms configured to evaluate trackable eye movements of the patient's eyes to detect different types of nystagmus, skew deviation, or subtle gaze abnormalities. This capability aids the practitioner in making a diagnosis.

The system 10 may run in network mode where the eyewear 12 is slaved to a remote unit. The system 10 may link to telestroke software. The system 10 may have the ability to communicate seamlessly with existing telemedicine softwares and hardwares, and can serve as an adjunctive device to existing services. By using mobile or WiFi-based internet, the software is compatible with existing telestroke apps and softwares and may connect to a telestroke cart wirelessly, such as through a Bluetooth connection. For example, instead of being run through a standalone application, the system 10 may be an added function of existing telemedicine apps, such as InTouch.

The system 10 may also include hardware such as a tablet PC with a touchscreen for the practitioner to use, sufficient RAM for the desired functioning, and the desired amount of storage. The software may also provide for two-way audio, in which case the system 10 may further include sound gear such as ear phones. The software may further include a video recording capability, database access for a patient's telestroke visual accessory history, and a voice-based text entry with learning mode. Many other optional features are possible and encompassed within the scope of the present disclosure.

Figure 10:
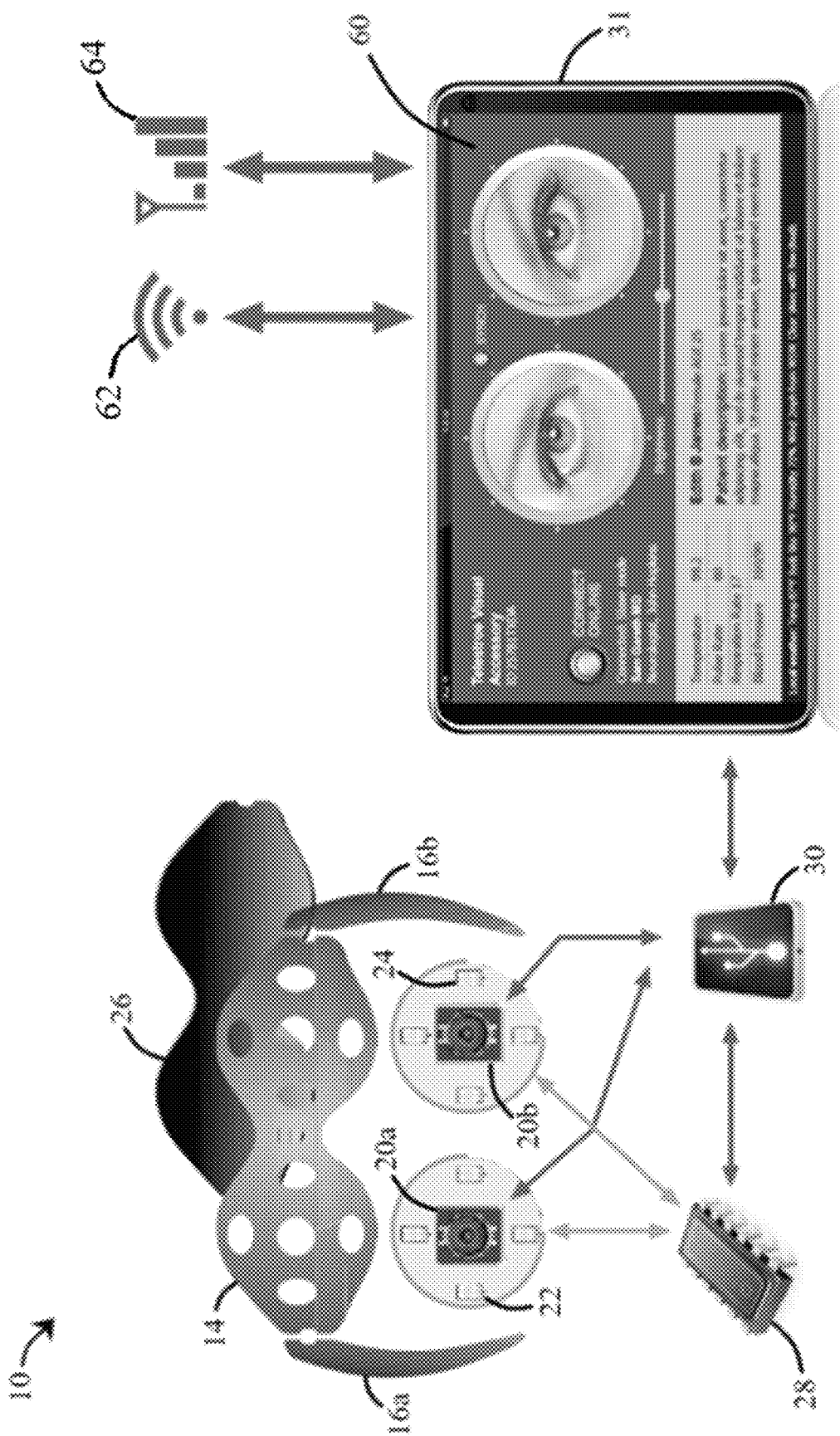
FIG. 10 Illustration of a system for telemedicine in accordance with the present disclosure.
Figure 11A:
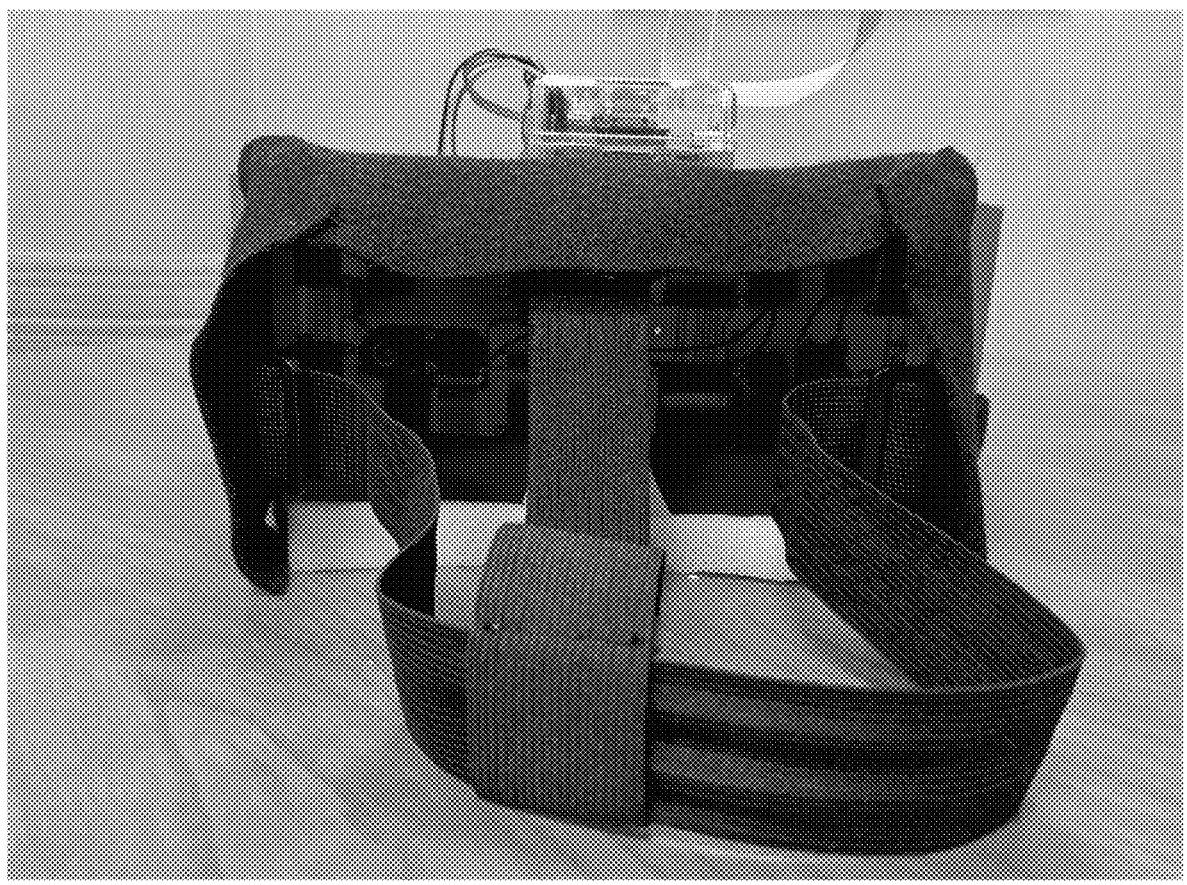
FIGS. 11A-11L Photographs of a non-limiting example telestroke eye examination accessory device in accordance with the present disclosure.
Figure 11B:
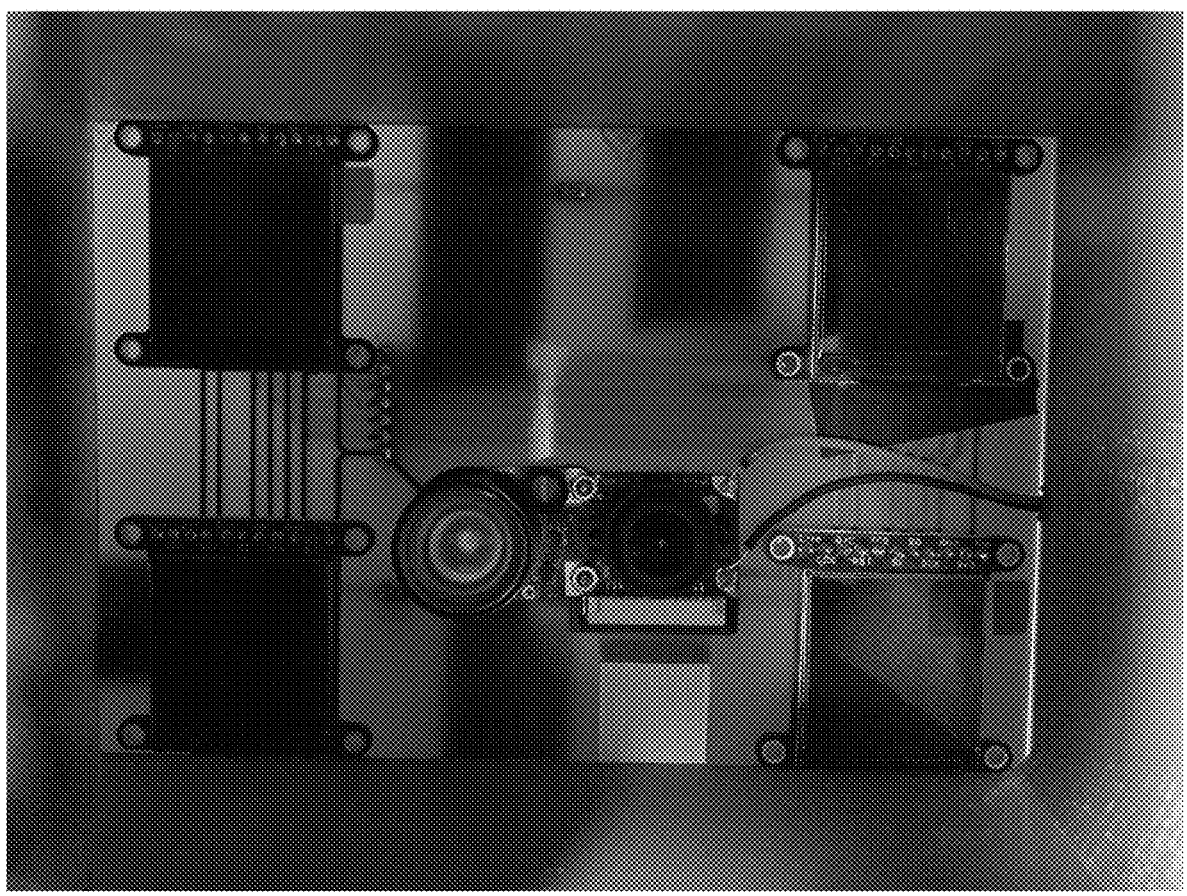
Figure 11C:
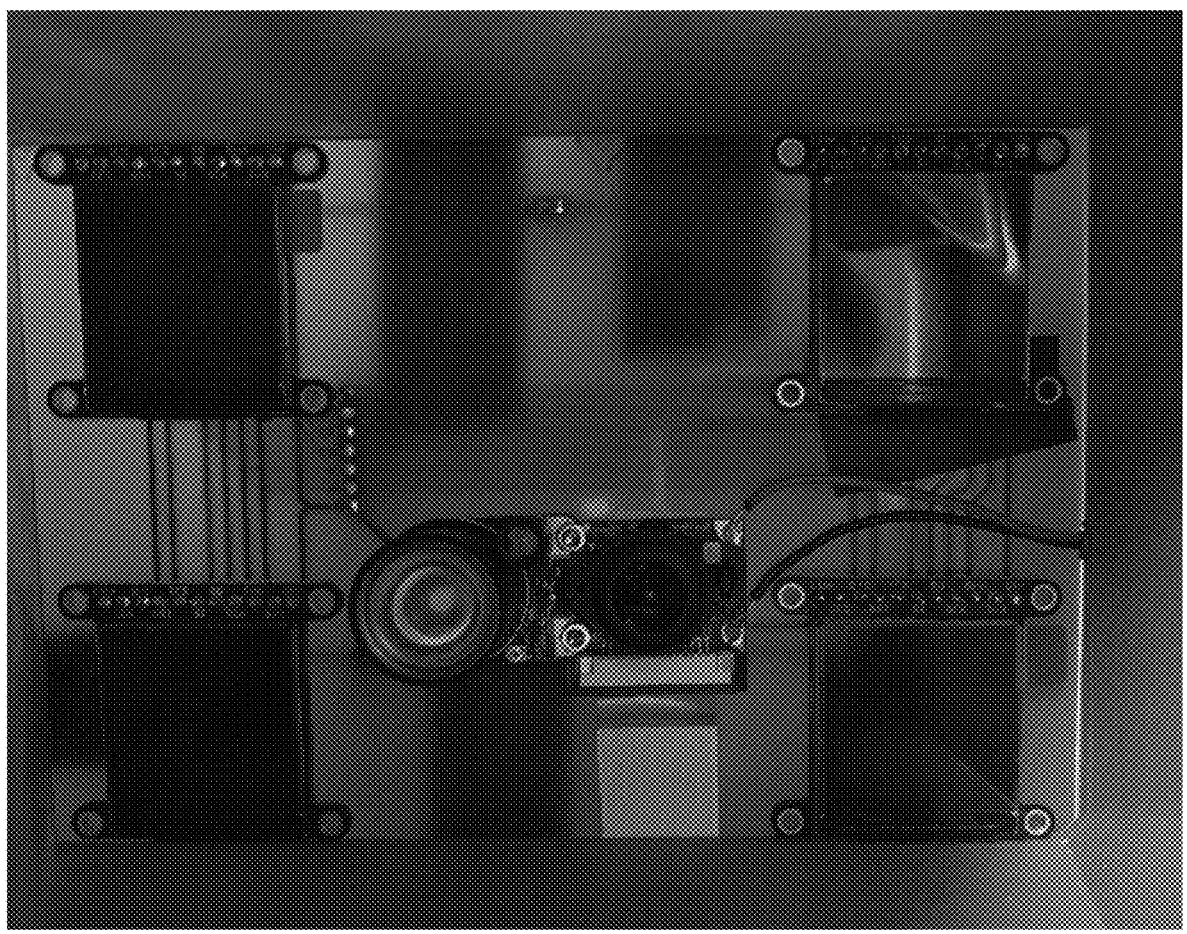
Figure 11D:
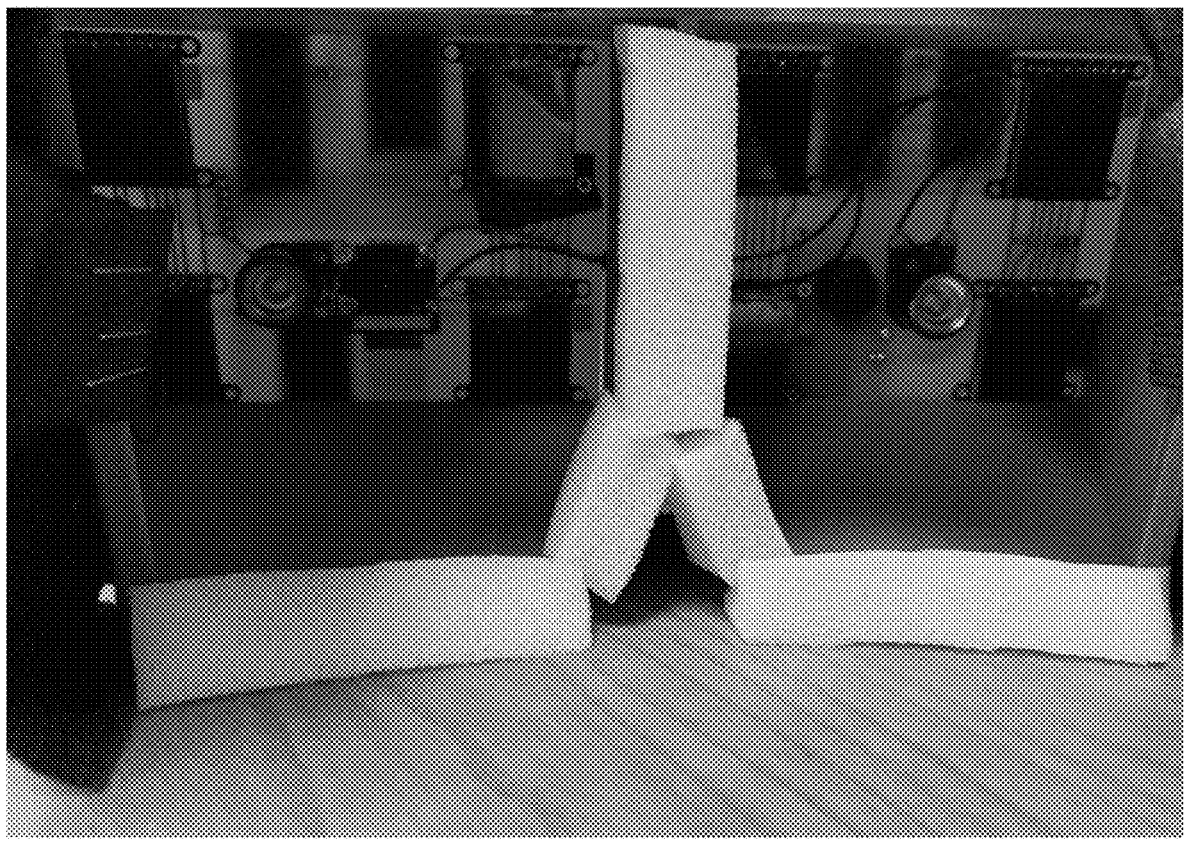
Figure 11E:
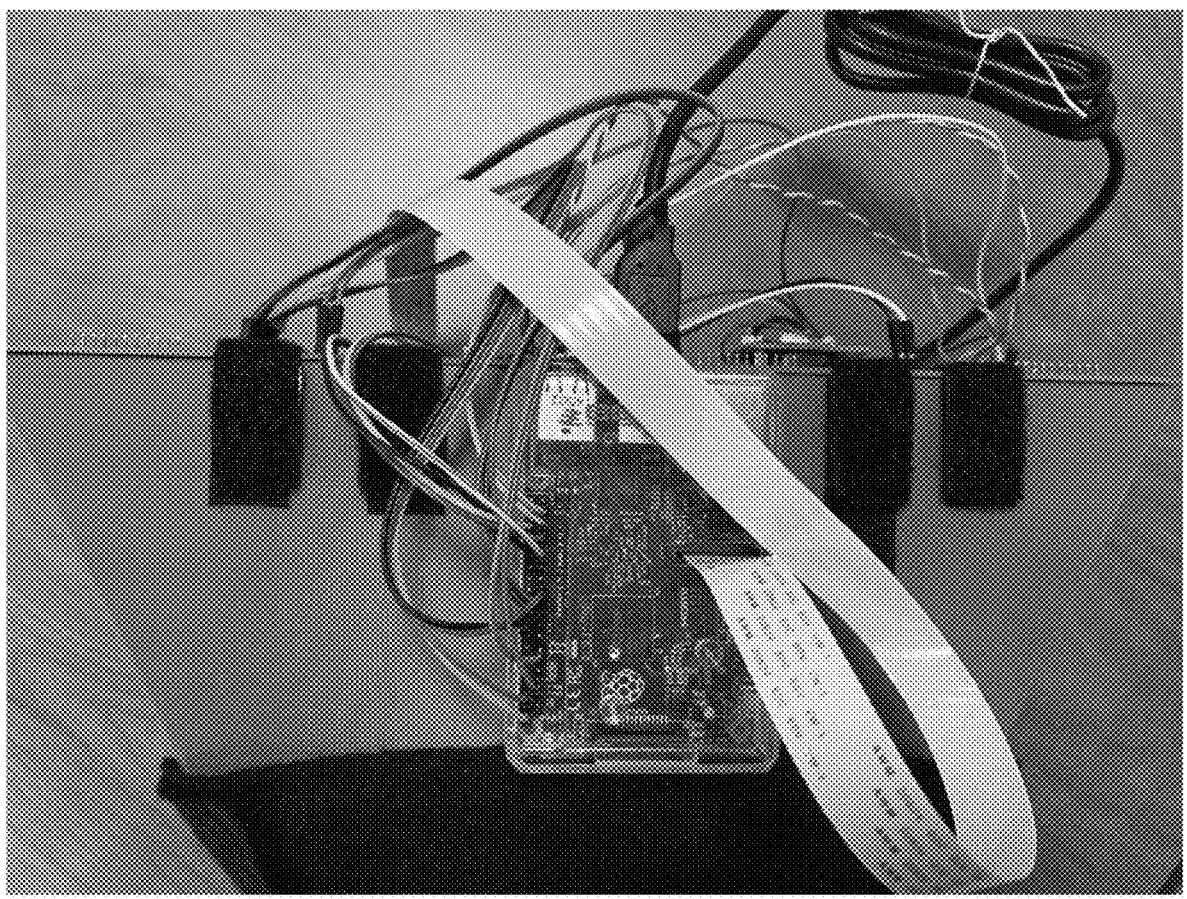
Figure 11F:
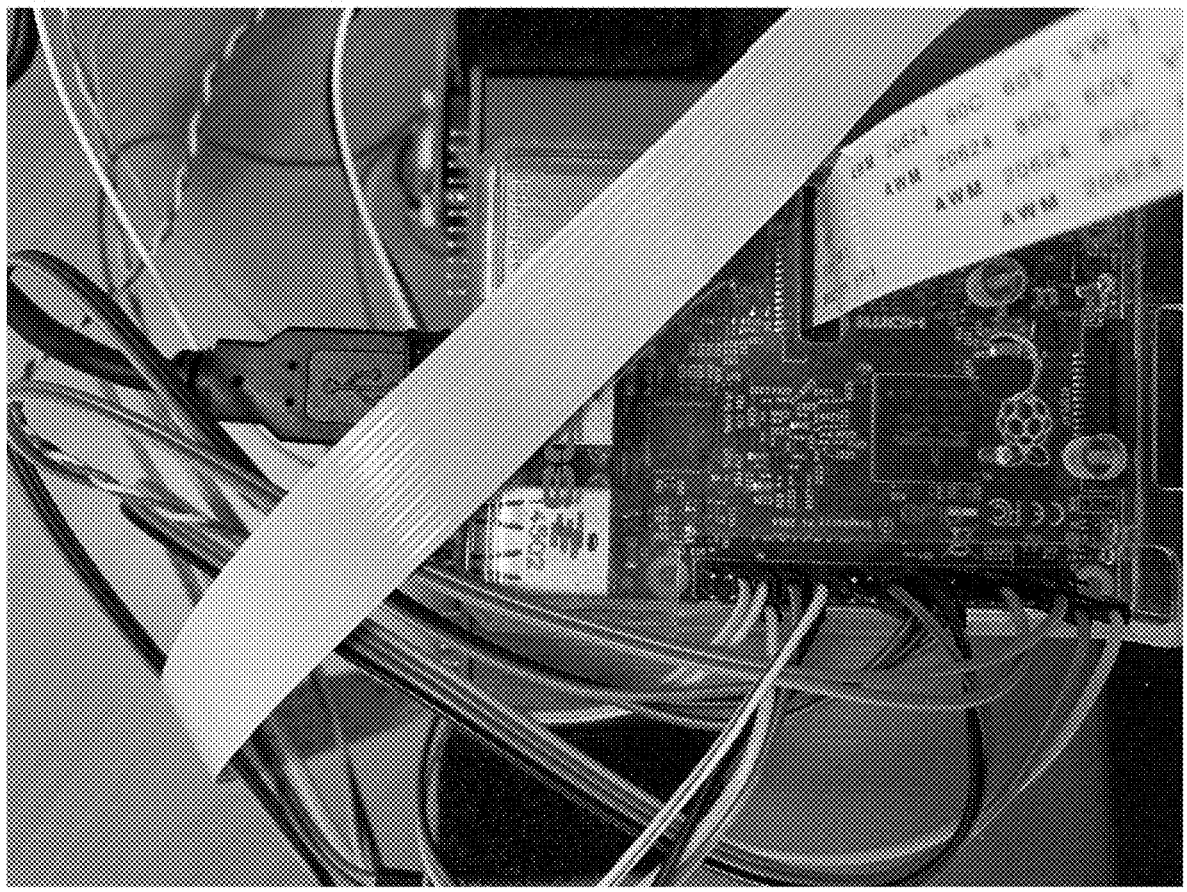
Figure 11G:
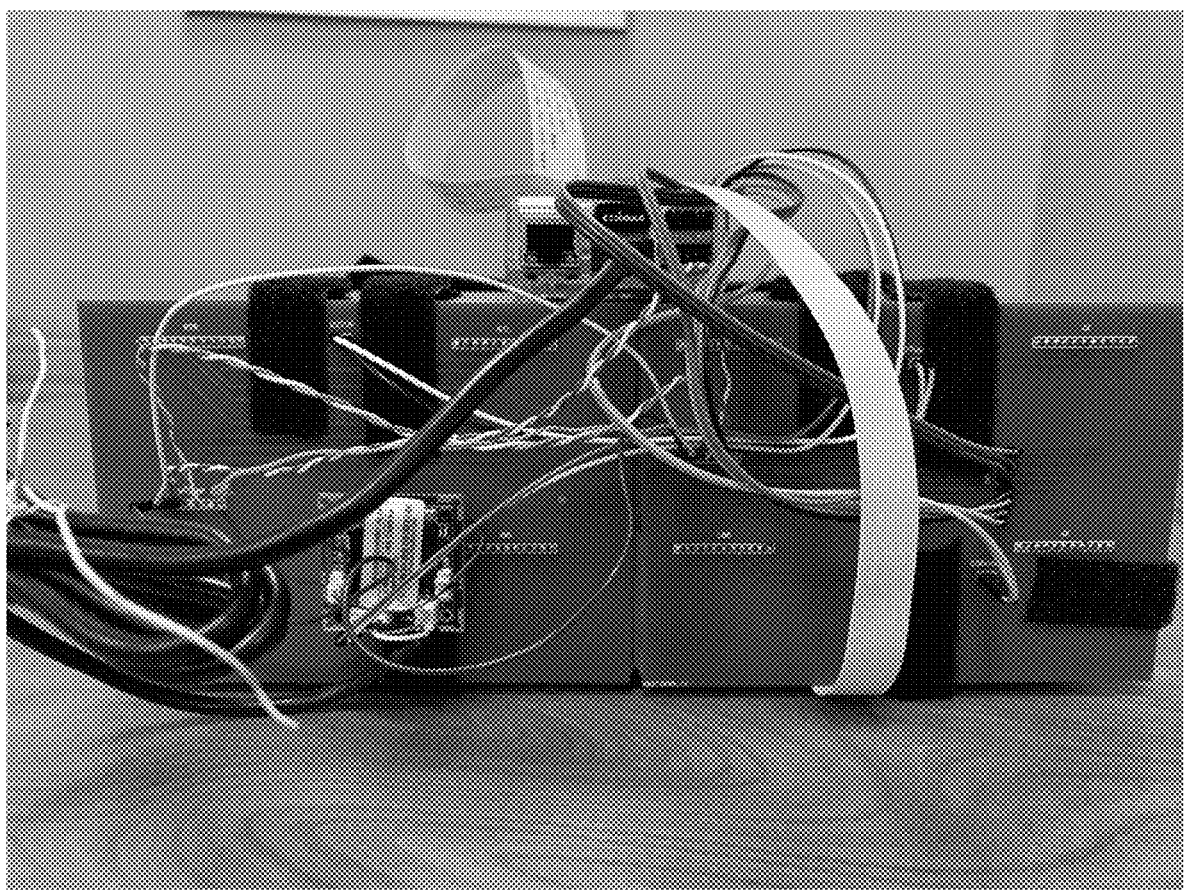
Figure 11H:
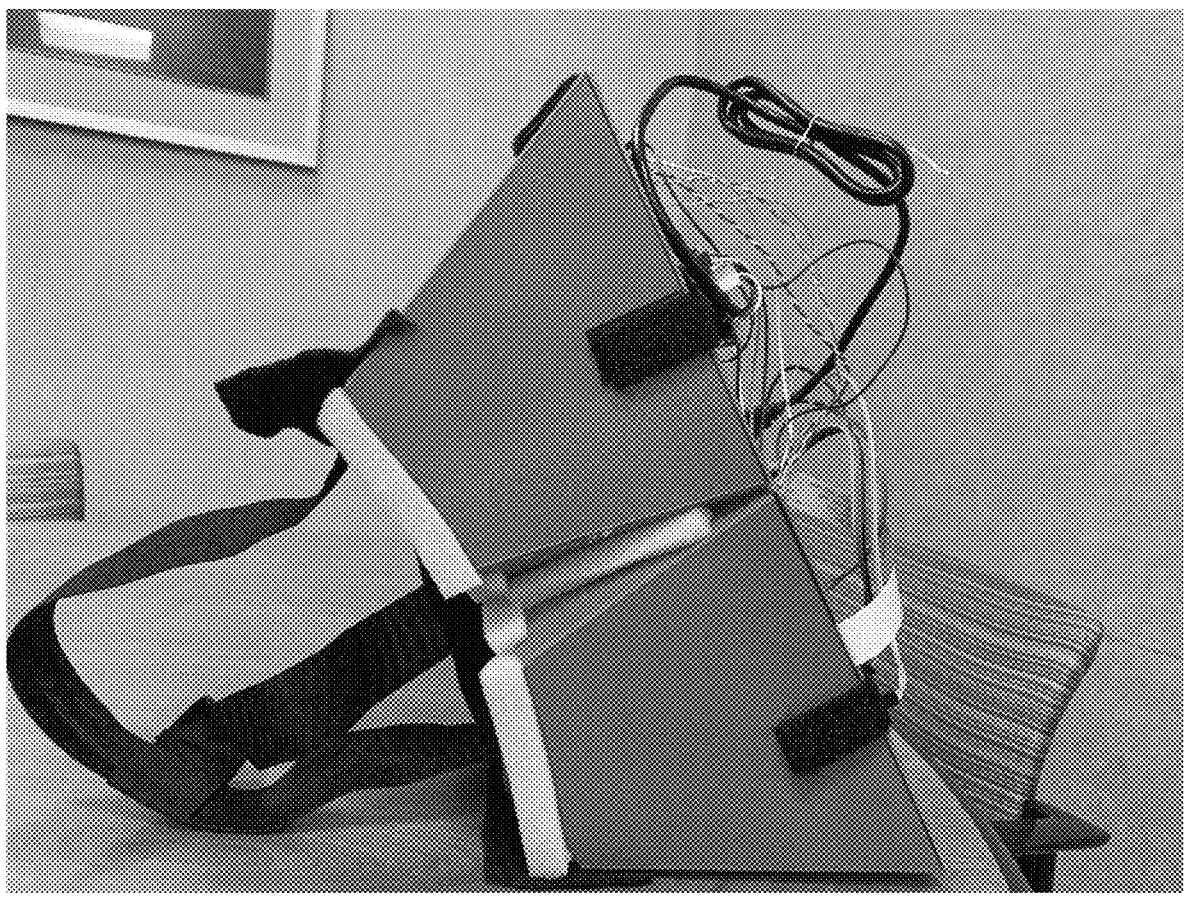
Figure 11I:
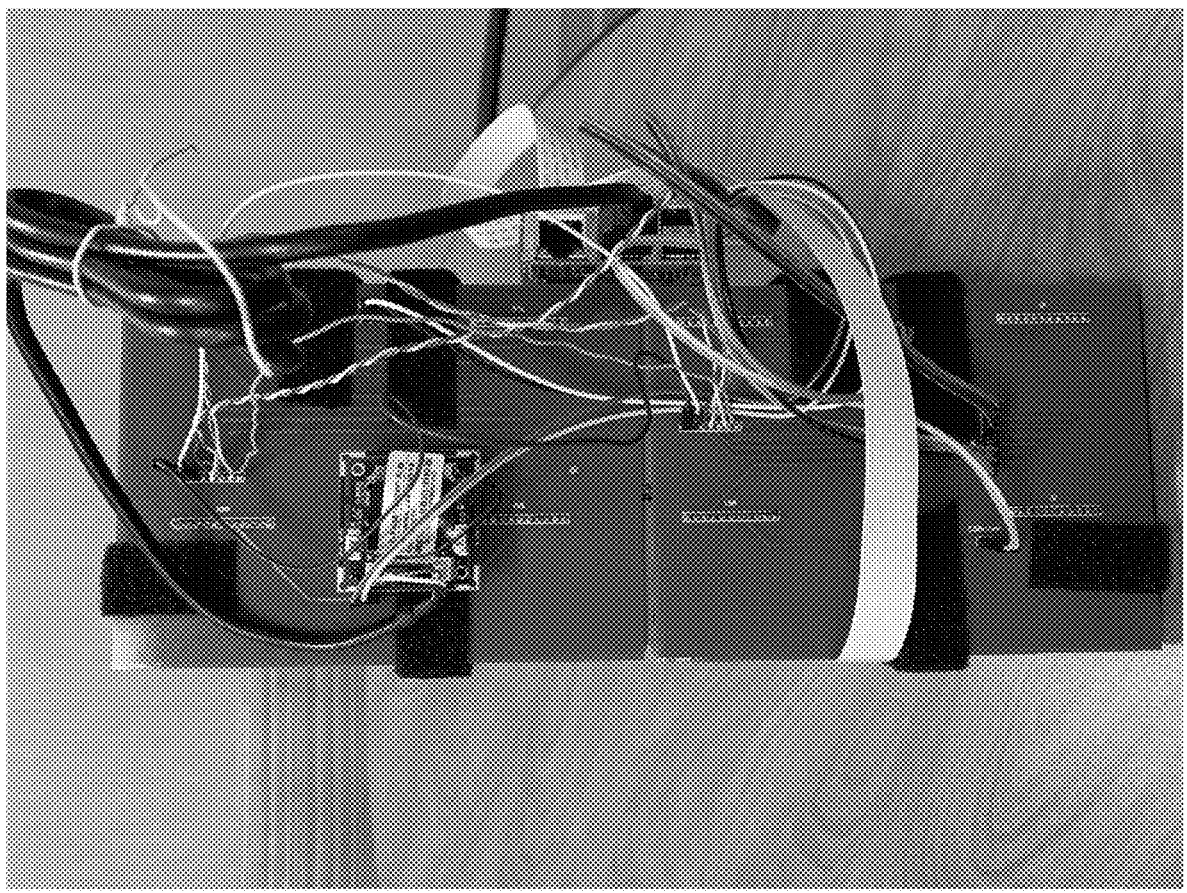
Figure 11J:
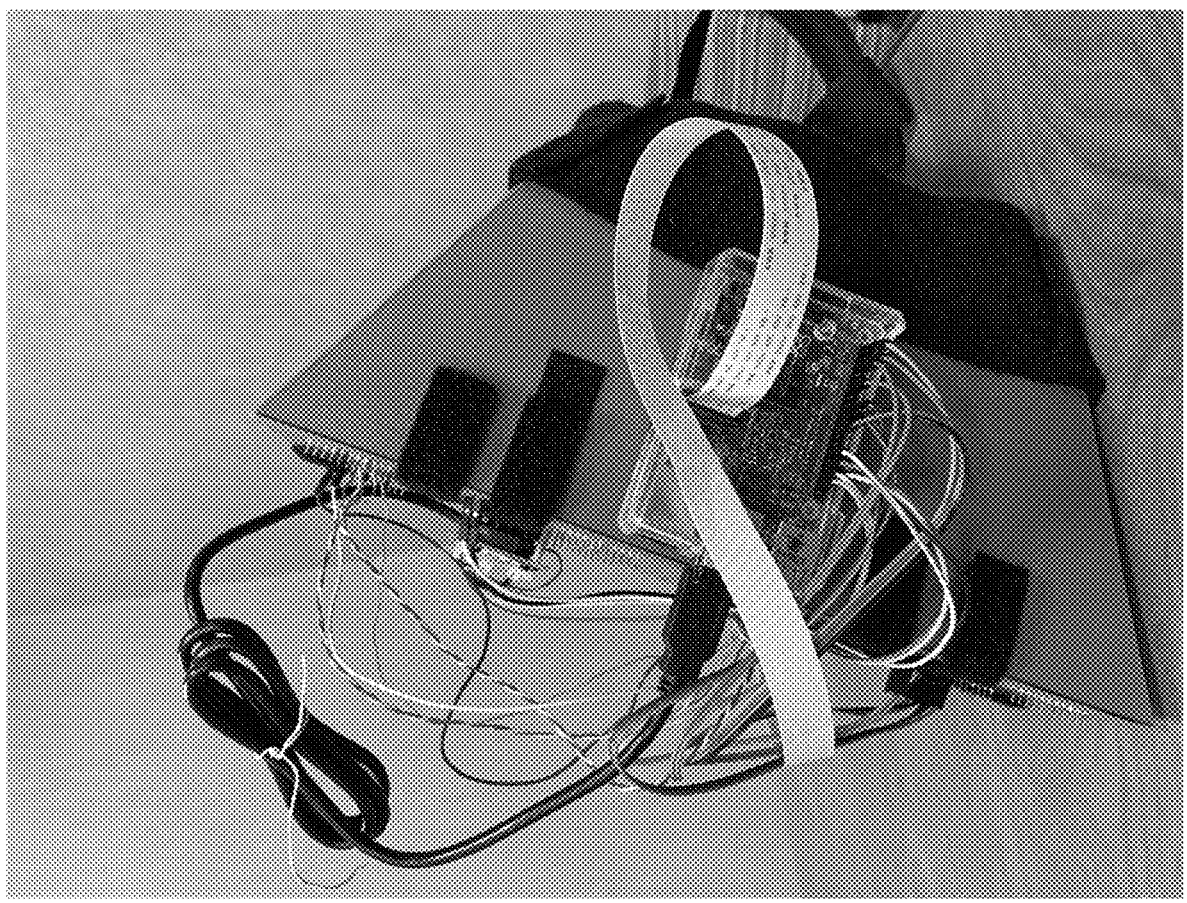
Figure 11K:
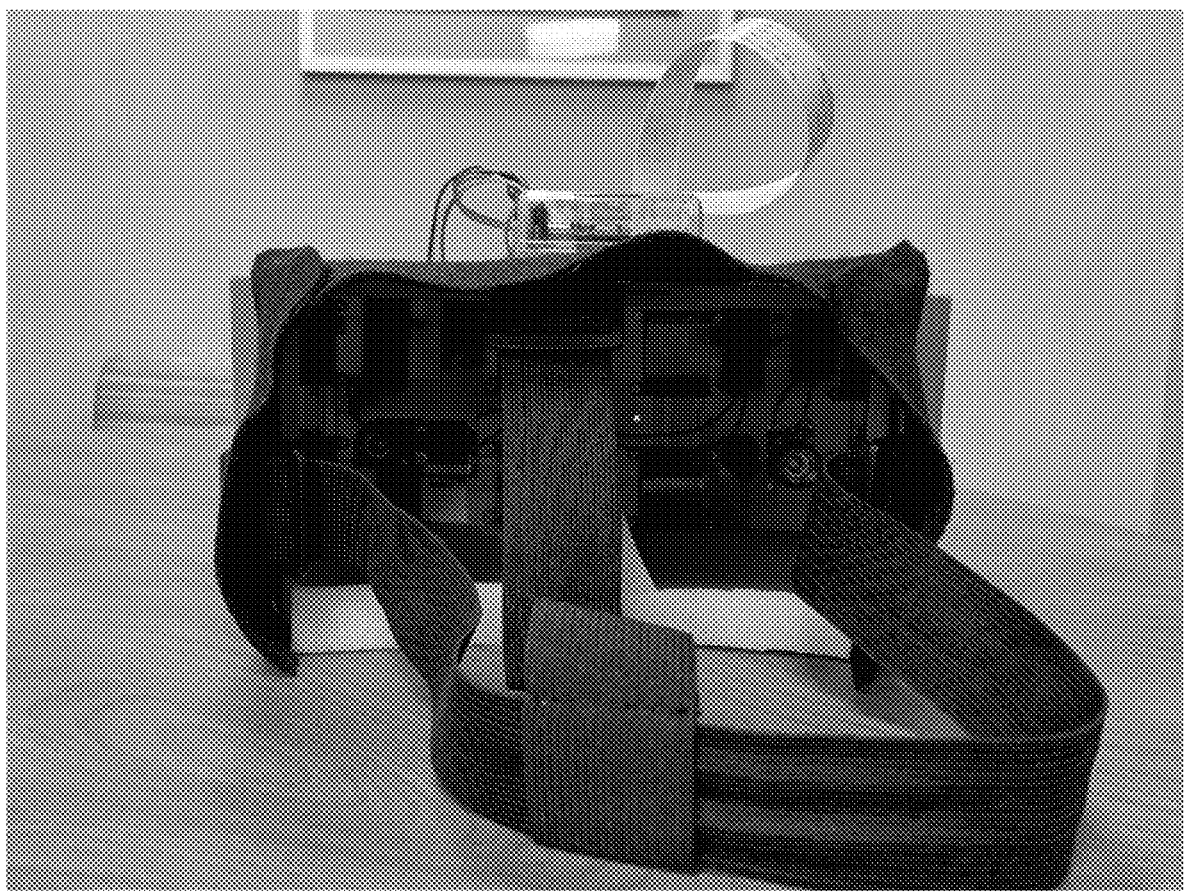
Figure 11L:
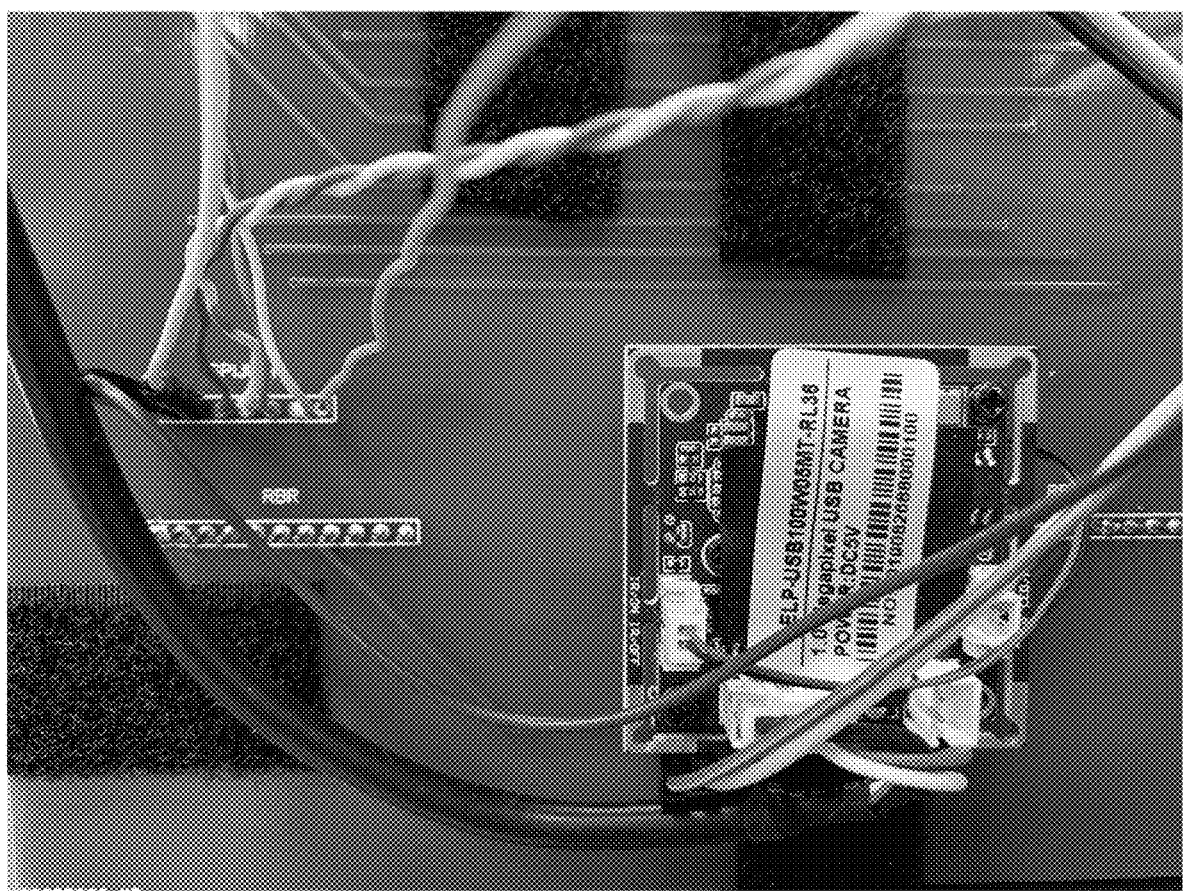

FIG. 10 illustrates a system 10 for telemedicine that includes the telestroke eye examination accessory device eyewear frame 14, darkening cover 26, light mixer 28, USB hub 30, smart device 31, and GUI 60. The system 10 may include the software and connectivity described herein, with the ability to connect to a WiFi network 62 or a cellular network 64.

The system 10 is a stroke detection tool for emergency medical respondents. The system 10 may be particularly useful in, for instance, an ambulance, hospital ERs, or transport helicopters. The system 10 may be operated by a neurologist or other stroke specialist who knows how to interpret the findings. The system 10 can be used in hospitals throughout the world, giving patients remote access to stroke specialists who can evaluate their symptoms in real-time with less reliance on bedside personnel for assistance. The system 10 may alleviate the problem of suboptimal evaluation of stroke symptoms. Strokes are time-critical, and the system 10 can save valuable minutes.

EXAMPLE

FIGS. 11A-11L show photographs of a non-limiting example telestroke eye examination accessory device. The example telestroke eye examination accessory device is configured to provide a dark environment for the wearer while exposing the wearer to arrays of lights in four quadrants around each eye, with a camera positioned in the center of each array of lights for monitoring the wearer's eyes. The example telestroke eye examination accessory device also includes a headband to secure the telestroke eye examination accessory device in place on a wearer's head.

Certain embodiments of the devices, systems, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A telestroke eye examination accessory device comprising: eyewear configured to be mounted on a patient's head, the eyewear comprising a frame defining a first eye well and a second eye well; a first camera in the first eye well; a first light array in the first eye well, wherein the first light array comprises a light in each of four different quadrants within the first eye well; a second camera in the second eye well; and a second light array in the second eye well, wherein the second light array comprises a light in each of four different quadrants within the second eye well;
wherein the first camera is equidistant from each of the four lights of the first light array, and wherein the second camera is equidistant from each of the four lights of the second light array.

2. The telestroke eye examination accessory device of claim 1, further comprising a power source configured to supply power to the first camera, the second camera, the first light array, and the second light array.

3. The telestroke eye examination accessory device of claim 1, wherein the first camera and the second camera are each IR cameras.

4. The telestroke eye examination accessory device of claim 1, wherein the first light array comprises LED lights, and the second light array comprises LED lights.

5. The telestroke eye examination accessory device of claim 1, wherein the first camera is positioned along a first centerline within the first eye well, and the second camera is positioned along a second centerline within the second eye well.

6. The telestroke eye examination accessory device of claim 5, wherein the first light array comprises two lights along the first centerline, and the second light array comprises two lights along the second centerline.

7. The telestroke eye examination accessory device of claim 1, further comprising a darkening cover disposed on the eyewear frame.

8. The telestroke eye examination accessory device of claim 1, wherein the telestroke eye examination accessory device is configured to communicate wirelessly with a telemedicine system.

9. The telestroke eye examination accessory device of claim 8, wherein the telestroke eye examination accessory device is configured to communicate with the telemedicine system via Bluetooth connection.

10. The telestroke eye examination accessory device of claim 1, wherein the eyewear comprises goggles that create darkness within the first eye well and the second eye well.

11. The telestroke eye examination accessory device of claim 1, wherein the first camera and the second camera are tracking cameras configured to identify abnormal eye movements.

12. The telestroke eye examination accessory device of claim 11, wherein vestibular testing algorithms are configured to provide objective data on abnormal eye movements and simplified visual field testing using a central fixation point.

13. A system for telemedicine comprising: a device comprising a graphical user interface displaying information about a patient; and eyewear in communication with the device;

wherein the eyewear comprises a first camera equidistant from each of four lights of the first light array, and a second camera equidistant from each of the four lights of a second light array;

wherein the eyewear is configured to illuminate lights in each of four different quadrants within each of two eye wells and provide to the graphical user interface a live stream of the patient's eyes while wearing the eyewear.

14. The system of claim 13, wherein a user may control the illumination of lights within the eyewear through the graphical user interface.

15. The system of claim 13, wherein the eyewear communicates wirelessly to the device.

16. The system of claim 13, wherein the live stream is provided by IR cameras within the eyewear.

17. The system of claim 13, wherein the first camera and the second camera are tracking cameras configured to identify abnormal eye movements.

18. The system of claim 17, further comprising software having vestibular testing algorithms for obtaining objective data on abnormal eye movements and simplifying visual field testing using a central fixation point.

19. The system of claim 13, further comprising artificial intelligence algorithms configured to evaluate trackable eye movements of the patient's eyes to detect different types of nystagmus, skew deviation, or subtle gaze abnormalities.

* * * * *